United States Patent [19]

Buckley et al.

[11] Patent Number: 4,576,286

[45] Date of Patent: Mar. 18, 1986

[54] PARTS SORTING SYSTEMS

[75] Inventors: Bruce S. Buckley, San Jose; Edward M. Buckley, Milpitas; Roy H. Reichwein, San Jose, all of Calif.

[73] Assignee: Cochlea Corporation, San Jose, Calif.

[21] Appl. No.: 508,121

[22] Filed: Jun. 27, 1983

[51] Int. Cl.⁴ .......................................... B07C 5/344
[52] U.S. Cl. ..................................... 209/558; 209/571; 209/576; 209/590; 367/87; 367/96; 367/902
[58] Field of Search ............... 209/555, 556, 558, 567, 209/570-572, 576, 590, 527; 367/8, 87, 96, 902, 7, 11, 99, 100, 103, 104, 123, 126, 151; 181/123; 73/602, 628

[56] References Cited

U.S. PATENT DOCUMENTS

| | | | |
|---|---|---|---|
| 3,438,493 | 4/1969 | Goble | 209/590 |
| 3,717,843 | 2/1973 | Farrah et al. | 367/105 X |
| 3,719,922 | 3/1973 | Lopes, Jr. et al. | 367/11 |
| 3,747,753 | 7/1973 | Flint | 209/555 |
| 3,757,285 | 9/1973 | Ferré | 96 X/ |
| 3,803,606 | 4/1974 | Lebail et al. | 367/8 X |
| 3,804,270 | 4/1974 | Michaud et al. | 209/564 X |
| 3,818,425 | 6/1974 | Peynaud et al. | 367/12 |
| 3,918,297 | 11/1975 | Rocha | 367/87 X |
| 3,975,261 | 8/1976 | Beck | 209/590 X |
| 4,049,123 | 9/1977 | Fegley et al. | 209/555 |
| 4,164,873 | 8/1979 | Böttcher et al. | 73/643 |
| 4,209,853 | 6/1980 | Hyatt | 367/11 X |
| 4,221,004 | 9/1980 | Combs et al. | 367/902 X |
| 4,223,790 | 9/1980 | Yoshida | 209/590 |
| 4,326,155 | 4/1982 | Griebeler | 367/96 X |

OTHER PUBLICATIONS

IBM Technical Disclosure Bulletin, vol. 18, No. 8, pp. 2665-2667, Affinito et al., Jan. 1976.

Primary Examiner—Robert B. Reeves
Assistant Examiner—Edward M. Wacyra
Attorney, Agent, or Firm—Robert Shaw

[57] ABSTRACT

A system for sorting parts wherein a part to be sorted is irradiated with wave energy of a single frequency (or very narrow band of frequencies) which interacts with the part. Wave energy emanating from the part is sensed at many spatially separated places to generate an electric signal representative of a characteristic of the amplitude and phase of the detected wave energy at each place. The electric signal so generated is compared with a pre-established signal and any differences therebetween are determined to establish whether the part is within acceptable limits in terms of geometric characteristics, e.g., size, material characteristics and orientation. The part is then acted upon on the basis of the comparison.

26 Claims, 14 Drawing Figures

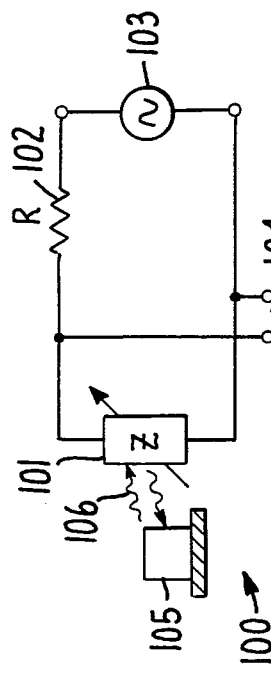
FIG._7A_.
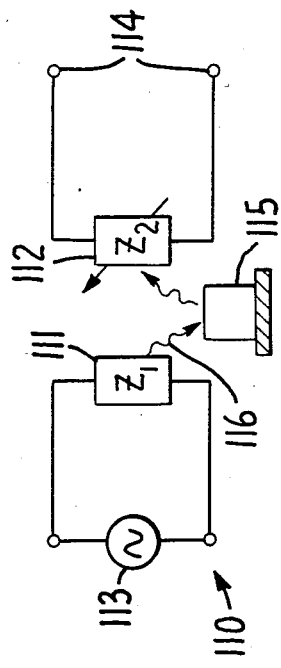
FIG._7B_.
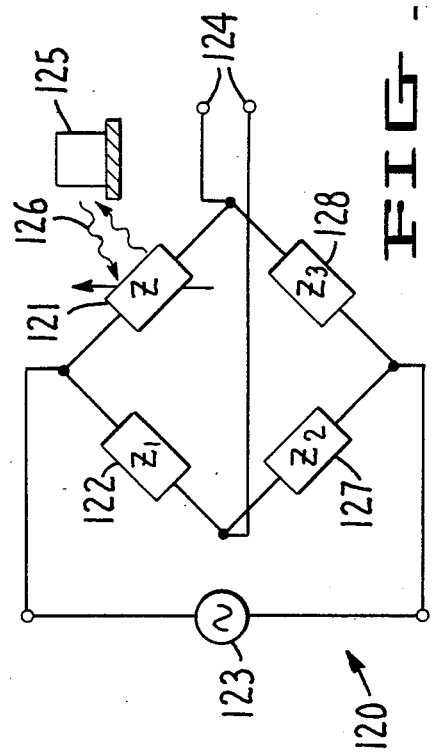
FIG._7C_.
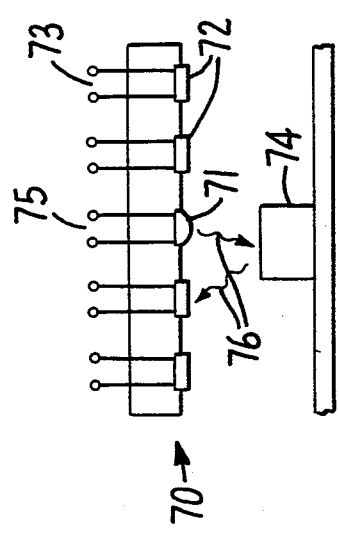
FIG._6A_.
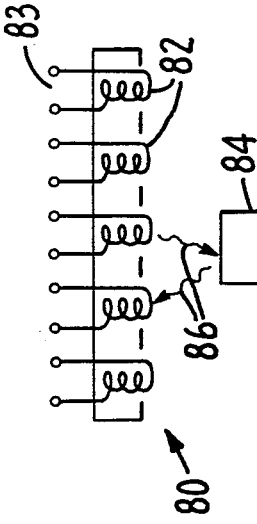
FIG._6B_.
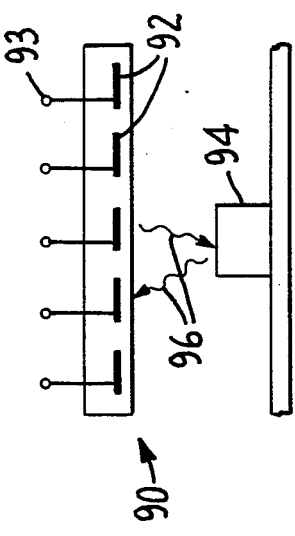
FIG._6C_.

PARTS SORTING SYSTEMS

BACKGROUND OF THE INVENTION

The present invention relates to parts sorting systems.

Attention is called to U.S. Pat. Nos. 4,095,475; 4,200,921; and 4,287,769 to the inventor B. Shawn Buckley herein.

In batch processing of the nature discussed herein, batches of parts from 50 to perhaps 1000 are processed at one time. Batch processing, which represents 75% of the dollar value of parts manufacturing, is economically appropriate for those parts which are made in volumes of less than a million parts per year. However, batch processing is a labor intensive approach that results in high cost per unit relative to automated parts manufacturing or hard automation.

In hard automation, the volume of parts processed is high enough that a machine can be built and dedicated to the manufacture of a particular part. Usually a million or more parts per year are needed to justify economically such a dedicated machine. It is called hard automation because "hard" tooling is needed to manufacture a particular part. If the design of a part should change, often another machine must be built to automate its manufacture, even for relatively minor changes in the part's design. Despite the drawback of requiring special-purpose machines for each part design, hard automation remains the most economical method of manufacturing when millions of a part are to be made.

"Soft" automation is an attempt to apply hard automation principles to batch processing: it replaces the "hard" tooling with electronic computers. The computers can be quickly reprogrammed to manufacture a part of a different design without performing the task manually or redesigning the machine that makes the part. In metal cutting, "soft" automation incorporates numerically controlled (NC) lathes and milling machines; in warehousing, it incorporates automatic retrieval systems; in paint spraying and spot welding it incorporates industrial robots; in factory automation, it incorporates programmable controllers.

However, in parts handling systems the versatility of "soft" automation has not been realized. True, industrial robots can be programmed to manipulate a part in enormously complicated ways once given a part to manipulate. But, unfortunately, it has no versatile way of obtaining the parts in the first place. Each robot comes equipped with custom-tooled parts feeders, whose cost is typically three to five times the cost of the robot itself. The parts feeders, the dominant cost in a robot parts handling system, must be custom designed and installed for each part a robot manipulates. Thus the robot becomes a mere accessory to what is essentially a hard automation system. While the robot is versatile enough to handle a variety of parts, the system to which it is coupled is not.

Vision systems represent an attempt by "soft" automation experts to couple the robot to the parts that it must handle. Unfortunately, vision systems are expensive compared to manual methods. Although they hold the promise of enabling a robot to feed its own parts, presently they are not a practical way to do so. A versatile low-cost method of feeding parts to robots is required before "soft" automation comes to parts handling in manufacturing.

Feeding parts to a robot, or for that matter a dedicated automation machine, requires that the parts be properly oriented. Parts usually come in baskets or bins, oriented randomly. The task of a parts feeder is to ensure that the parts are presented to a robot in the same way for each part. For example, the cap of a ball point pen must be presented to a robot in a particular orientation for the subsequent mating to the body to occur properly.

In addition to orienting parts for soft or hard automation, inspection of the parts is also important. In hard automation, defective subcomponents can double the cost of assembling a typical component. The difficulty is downtime: defective parts jam a machine and require operator time to fix the jam. Stopping production to unjam a machine reduces the production rate significantly—enough to justify the highest quality parts. But high quality parts themselves are expensive so a compromise is reached between the increased cost of high quality parts and the increased cost of unjamming machines.

If low-quality parts were sorted prior to assembly by a dedicated automation machine, significant saving would result. Downtime due to jams would be eliminated, production rates would increase and manufacturing costs would be reduced. Robots used in manufacturing of parts could also benefit from using pre-sorted parts: jams in robot-based systems can often result in damage to the robots.

Accordingly, it is an objective of this invention to provide a parts orienting device which automatically feeds similar objects to an inspection region, detects their orientation through various sensors, and manipulates the objects to ensure that objects leaving the orienting device have only the desired orientation.

Another objective of the invention is a parts-sorting device which automatically feeds similar objects to an inspection region, detects the shape of the objects through various sensors and manipulates the objects to ensure the objects leaving the sorting device have only the desired shape or other sensed characteristics.

These and still further objectives are addressed hereinafter.

The foregoing objectives are achieved, generally, in an apparatus for sorting parts for the purpose of interfacing with an industrial robot or the like or for presenting those parts to a production machine or the like. A feeder transports a part into a sensing region where it is subjected to wave energy of a single or narrow-frequency band. Reflected or other wave energy resulting from the impinging wave energy is sensed at a multiplicity of places to provide signals from which amplitude information and phase information of the received wave energy can be derived with respect to each place. An analyzer extracts from the amplitude information and the phase information intelligence with respect to a geometry parameter and/or electromagnetic parameter the part, which, in turn, is used to sort the part. It will be appreciated that the geometry or electromagnetic parameters includes position data as well as shape data with respect to the irradiated part.

The invention is hereinafter described with respect to the accompanying drawing in which.

Figure 8:
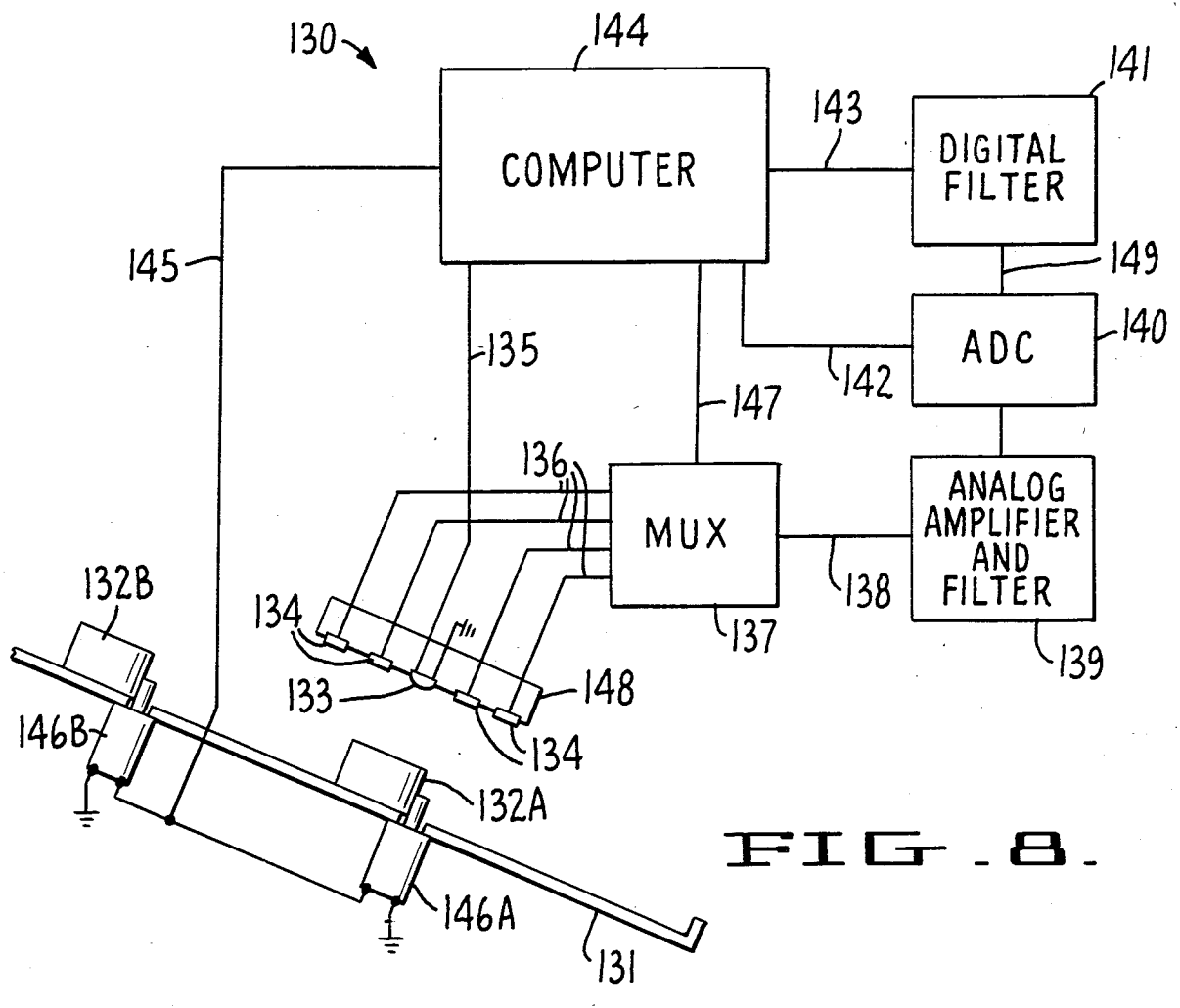
Figure 9:
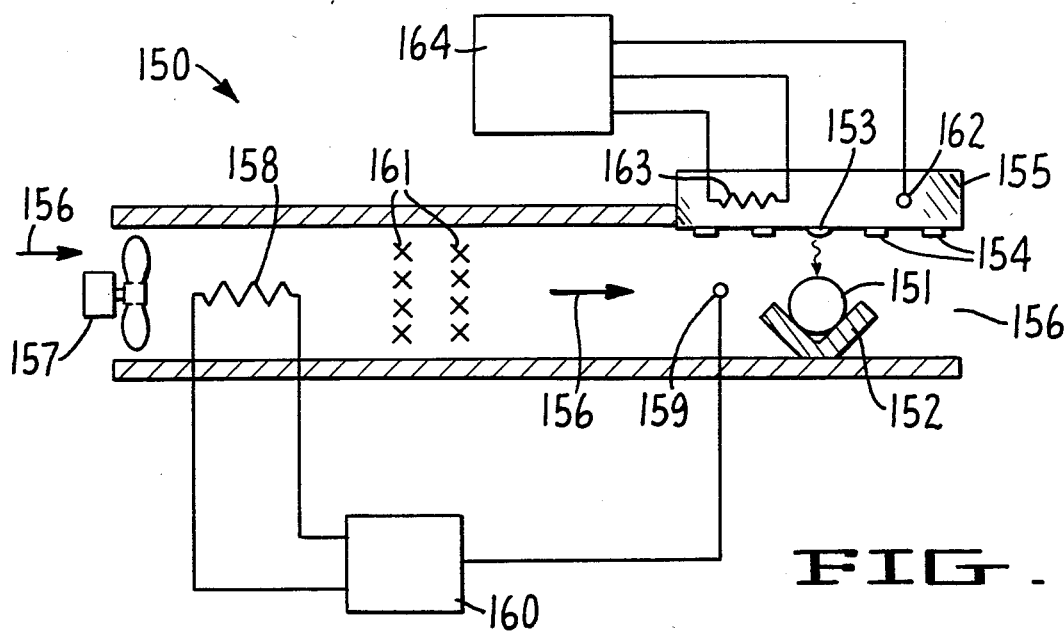

FIGS. 6A, 6B and 6C each show diagrammatically a wave energy transmitter to irradiate a part and receiver-transducers to receive wave energy from a part, evoked by the radiation impinged thereon;

FIGS. 7A, 7B and 7C show schematically circuitry for implementing sending-receiving functions in FIGS. 6B and 6C;

FIG. 8 is a diagrammatic representation of one form a parts-sorting system can take, detailing the electrical circuitry; and FIG. 9 shows diagrammatically a scheme to improve certain aspects of the apparatus in the earlier figures, some parts in the figure being shown as a side section view.

Figure 1:
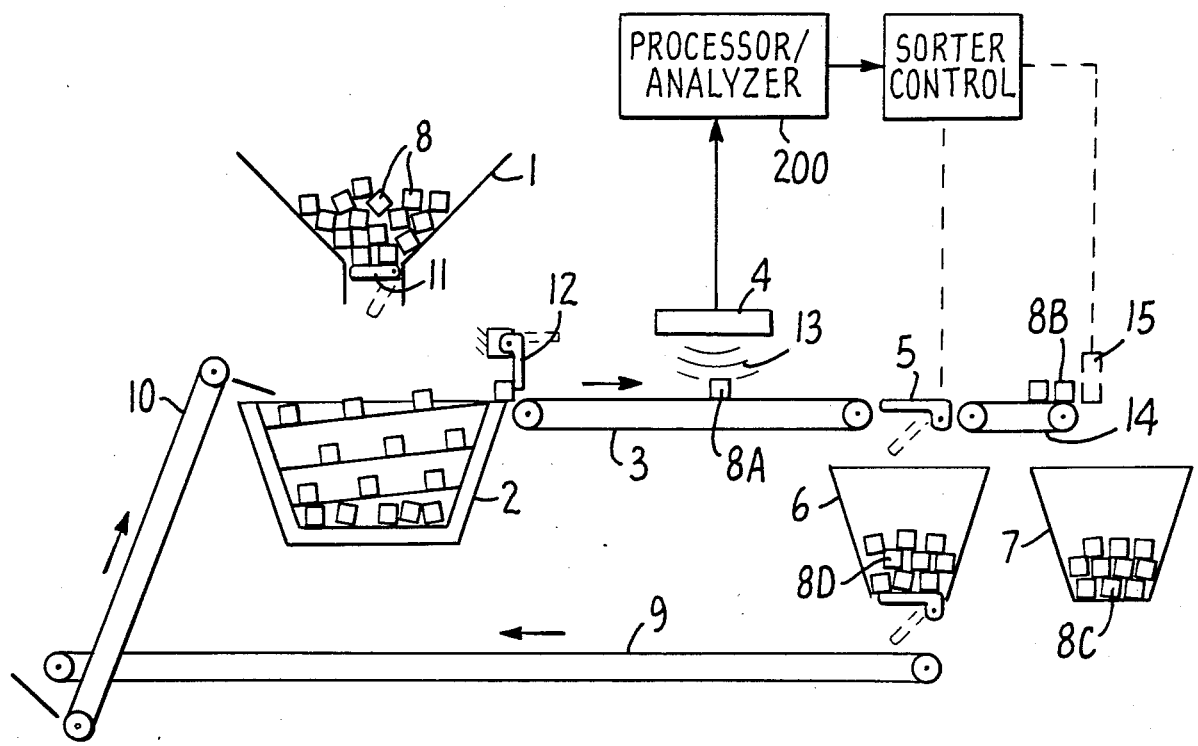
FIG. 1 is a diagrammatic representation of a parts feeding and sorting system embodying the present inventive concepts and showing one arrangement in the form of discrete element feeding, sensing, analyzing and sorting parts.

The present invention, schematically as shown in FIG. 1, consists of five basic elements: a parts storage device 1; a parts feeder 2; a wave energy emitter and sensor 4; a processor/analyzer 200; and sorting mechanisms. The parts storage device 1 that holds a number of the objects 8 (also identified as 8A, 8B . . . ) which are to be sorted or oriented. An electrically actuated gate 11 on the hopper 1 feeds parts 8 into the feeder 2. The feeder 2 shown is a bowl feeder, known for its ability to feed a variety of parts 8 with little, if any, modification of the feeder for a new shape of part 8. The hopper gate 11 is set to feed parts from the hopper 1 (when the feeder 2 runs out of parts 8) via a fill paddle, not shown to simplify the figure. Such an arrangement of feeder 2 and hopper 1 with automatic fill between the two is standard in the industry. (Another variation of feeder 2 is a belt feeder with its attendant storage hopper similar to the hopper 1.)

The purpose of the feeder 2 is to move the parts to a transfer mechanism 3 to convey the parts 8 under a sensing mechanism 4 (the sensing mechanism 4 both transmits and receives wave energy). In general, the parts 8 must be fed one at a time to the sensors 4; so often an escapement 12 is necessary. An escapement allows one object 8 (e.g., 8A or 8B . . . ) to move to the sensing region 13. In some cases, the feeder 2 itself acts to only allow one part 8 at a time to move the sensing regions by a process called singulation. In other situations, the transfer mechanism 3, shown in FIG. 1 as a belt, can act to separate the parts 8 by accelerating the parts 8 as they move to the top of the feeder 2. If the parts 8 move along the transfer mechanism 3 faster than they arrive from the feeder 2, the tendency will be to separate the parts 8 one from another. (Other ways to separate the parts 8 so they arrive one at a time include rotating brushes and air jets which accelerate the parts thereby separating them, much as does the belt described.)

When individual parts (e.g., the part 8A) arrive at the sensing region 13, the sensors 4 transmits continuous acoustic and/or electromagnetic wave energy of a single (i.e., narrow band) frequency into the sensing region where the wave energy interacts with the part 8A and is reflected to the sensors 4. The sensors 4, as later discussed, consists of a multiplicity of sensors that receive the wave energy after interaction with the part and sense the shape of the part or its orientation by means of acoustic and/or electromagnetic wave information, as described in the above-mentioned Buckley patents. The sensing mechanism is discussed later with reference to the prior Buckley patents; analysis is effected in the processor/analyzer 200 which may, in part, be a microcomputer or the like, to provide sorting signals.

Once the shape or orientation of the object 8A has been determined, the part proceeds to a rejection gate 5 which may be actuated by signals from the unit 200. If the part 8A is found to have the proper shape or orientation, it proceeds to a parts presentation point via a transfer mechanism 14 (shown in FIG. 1 as a belt conveyor) where the part is labeled 8B. In robot operations, the part 8B is held in its proper orientation by a stop 15 for pickup by a robot, not shown. In some other robot operations, parts 8A are taken from the parts presentation point without the interaction of the rejection gate 5; the robot simply changes its actions based on the shape or orientation. In automated manufacturing operation, the transfer mechanism 14 would deliver the properly shaped and oriented part 8B directly to the dedicated automation machine, not shown. In parts sorting operations, the transfer mechanism 14 can simply deliver the parts 8B of the correct shape to a bin 7 where correct parts are designated 8C.

Meanwhile, parts of incorrect shape or orientation (marked 8D) are rejected from the transfer belt 14 by the gate 5. In a parts sorting operation, the parts 8D can be simply stored in a bin 6. In robotics or hard automation applications where proper part orientation is required, the parts 8D which are correct parts (though improperly oriented) are transferred to other transfer mechanisms 9 and 10 so that parts of correct shape but incorrect orientation may be returned to the feeder 2. Once the parts 8 are returned to the feeder they are randomly oriented so that they may be subsequently fed to the parts feeder mechanism 14, should the new orientation be correct.

Figure 2:
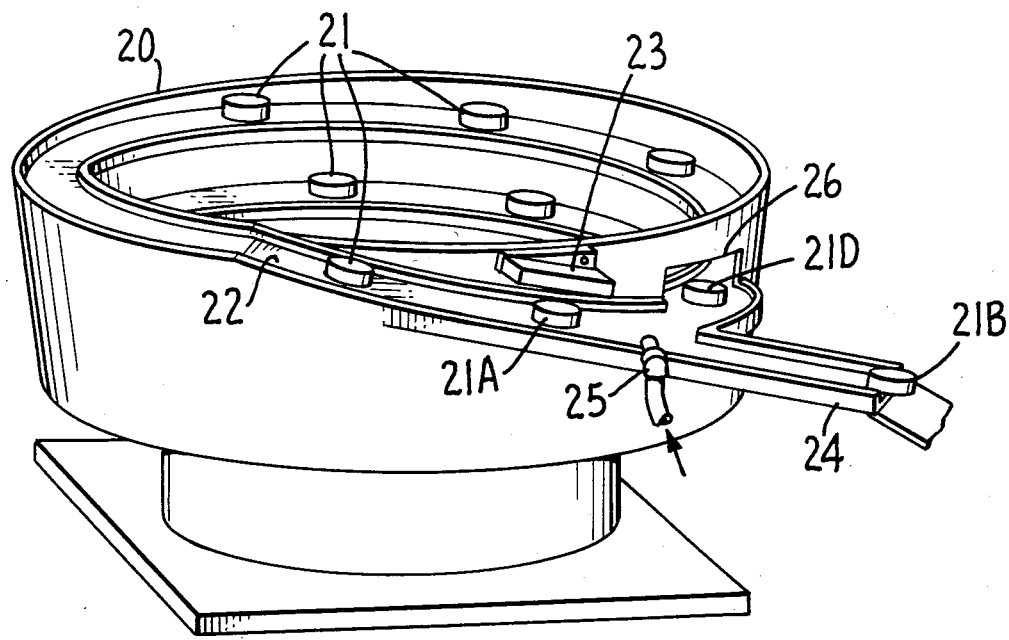
FIG. 2 is an isometric view of a modification of the system of FIG. 1, showing some of the discrete elements of the parts feeding mechanism in the earlier figure combined in one element.

In FIG. 1, the various mechanisms have been separated to elucidate their functions. In an actual sorting or orienting device, some of these mechanisms can be combined to give the appropriate functions. For example, the transfer mechanisms 3, 9, 10, and 14 in FIG. 1 are more easily designed as gravity chutes which take a part from the top of the feeder and divert it either to a parts presentation stop or back to the feeder as shown in FIG. 2.

Parts 21 in FIG. 2, travel to the top of a vibratory bowl feeder 20 and then slide down a gravity chute 22 to an inspection region below a sensing mechanism 23. A computer (not shown) analyzes the sensor signals from the sensing mechanism 23 and actuates a part rejection mechanism 25. In this case, an air jet is a method by which a defective part 21D or an improperly oriented part is diverted from a gravity chute 24 back into the bowl feeder 20. Such parts 21D typically re-orient themselves on a successive journey up the spiral inner track of the feeder 20. A hole 26 through the side of feeder 20 allows re-introduction of defective or misoriented parts 21D back into the feeder 20. In some situations, defective parts 21D are distinguished from misoriented parts 21D and subsequently fed to a reject parts bin via a diverting mechanism such as the air jet 25.

Figure 3:
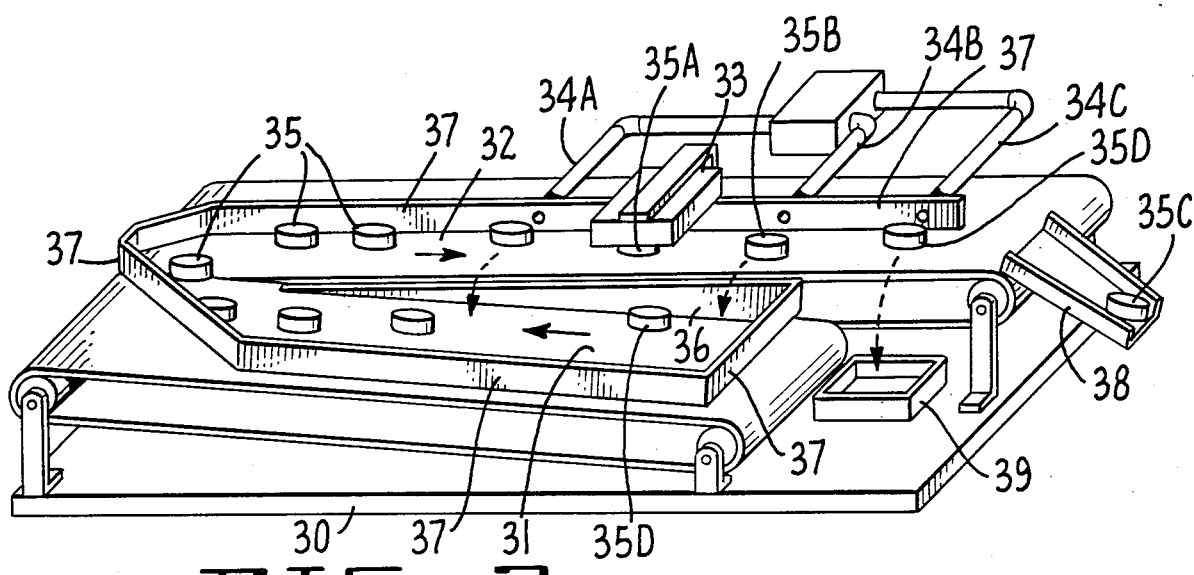
FIG. 3 is an isometric view of a further modification.

Another variation of the same parts feeding and orienting apparatus is shown at 30 in FIG. 3 where parts are marked 35, 35A–35D. In FIG. 3 a belt feeder, similar to one sold industrially by the Page-Wilson Corporation, of Bridgeport, Connecticut, combines the transfer mechanism 3, 9, 10 and 14 of FIG. 1 but without an intermediate feeder 2. The feeding/orienting system 30 has an automated parts hopper (not shown for clarity) which maintains an adequate supply of the parts 35 on a main belt 31. Essentially the feeder/orienting system has two belts 31 and 32 which circulate parts 35 within the confines of a fence 37. The main belt 31 is inclined as will be discussed shortly. Parts 35 travel up the main belt 31 and onto the secondary belt 32.

A sensor mechanism 33 senses the shape or orientation of the parts 35. Parts of the wrong orientation or defective parts 35B are diverted back onto the main belt 31. Shown here is an air jet 34B which is actuated by a computer (not shown) when the sensor signals from the sensing mechanism 33 indicates the improper orientation of a part 35B. Diverted parts 35B tumble over a step 36 and re-orient themselves such that on subsequent passes past the sensing mechanism 33 they have a possibility of passing onto the gravity chute 38. The chute 38 can be a parts presentation chute for a robot so correctly oriented parts 35C can be grasped by a robot. Alternatively the chute can feed properly oriented parts 35C directly to a hard automation manufacturing machine (not shown).

Other variations of the parts feeding and orienting system 30 can improve its usefulness. A diverting mechanism, in this case an air jet 34A, can insure that only a single part 35 at a time enters the sensing region below the sensing mechanism 33. Thus, if parts 35 travel down the secondary belt 32 too fast for proper sensing, the sensing mechanism 33, via the computer, can command the air jet 34A to actuate until sensing is complete.

Diverting mechanism 34C, in this case an air jet, may be used to reject defective parts 35. If a defective part 35D is sensed by the sensing mechanism 33, the air jet 34C is actuated by the computer to divert the defective part 35D into a reject part bin 39.

Figures 4, 5A:
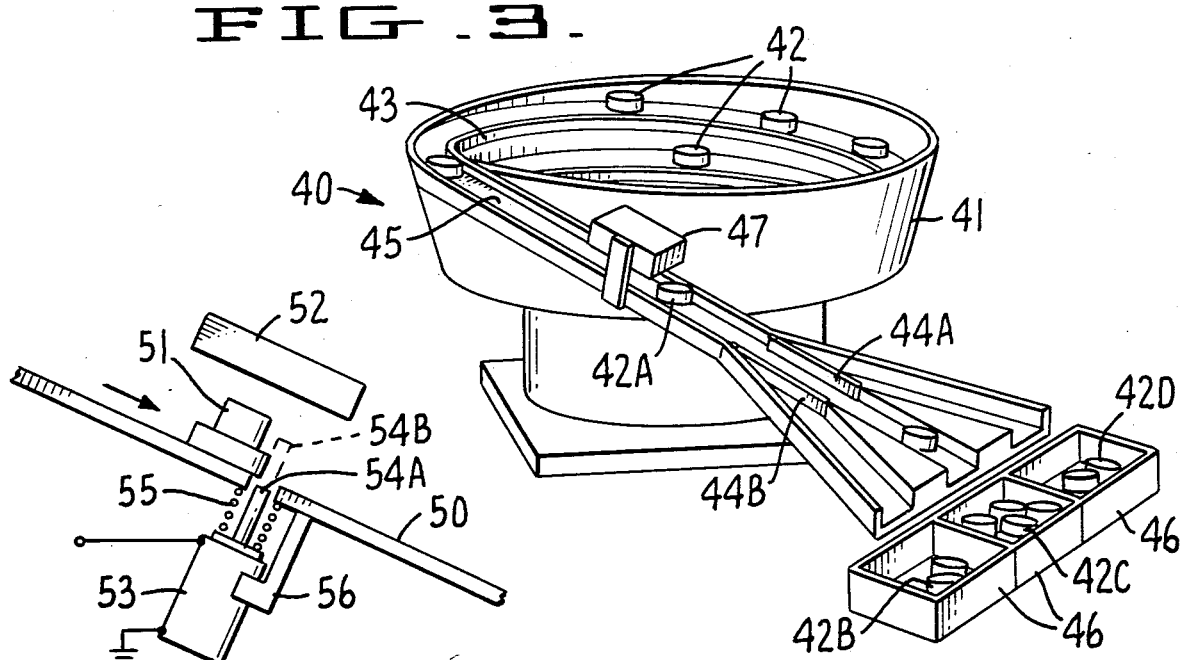
FIG. 4 is an isometric view of a still further modification, which, like FIGS. 2 and 3, mainly is intended to show another scheme for moving parts about.
FIGS. 5A and 5B show diagrammatic side and top views of mechanisms to stop parts during a sensing operation.

Another variation of the present invention is a parts sorter 40, as shown in FIG. 4, in the form of a bowl. Here a parts feeder 41 brings parts 42 to the top of the bowl. An accompanying parts hopper, such as the hopper 1 in FIG. 1, can be added to insure an adequate supply of parts 42 arriving at the top of the bowl. An escapement or singulation mechanism 43 allows only one part 42A at a time to slide down a chute 45 and beneath a sensing mechanism 47. The computer (not shown) analyzes the shape of the part 42A and actuates gates 44A and 44B depending on the analysis of the sensor signals from the sensing mechanism 47. Parts 42B of one shape are diverted by gates 44A and 44B into one bin 46 while parts 42C and 42D of other shapes are diverted into other bins 46.

The shapes can be correct parts and incorrect parts, or the parts may be sorted according to other criteria. For example, the parts 42B can be coins of one denomination while parts 42C and 42D can be coins of other denominations. On the other hand, the parts 42B can be threaded fasteners such as screws with threads while the parts 42C can be the same screws but without threads. In either case, the parts are sorted in various categories on the basis of shape or electromagnetic characteristics.

It will be noted that the system 40 is primarily a parts sorter rather than a parts orienter. Usually parts of incorrect orientation must be tumbled and recycled to some sensing mechanism as are the parts 8D in FIG. 1, the parts 21D in FIG. 2 and the parts 35D in FIG. 3. However, in the system 40, no mechanism exists for transporting correct parts, but of the wrong orientation, back to the bowl 41. If required, cogged belts (such as the belt 10 in FIG. 1) may be used for those parts orienting applications where correct but misoriented parts must be returned to the parts feeder.

Figure 5B:
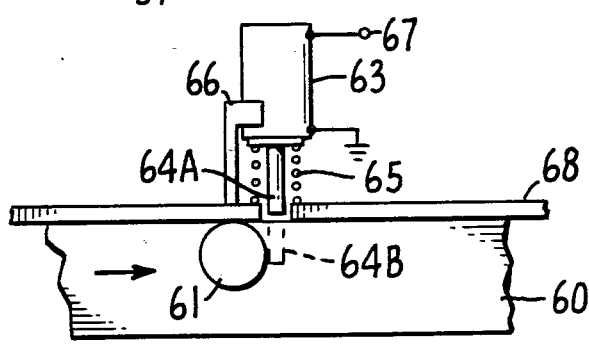

The sensing mechanisms in FIG. 1–4 require that the parts being sensed are not moving for the highest accuracy measurement of the part's shape. In these applications a part-stop mechanism can be positioned to stop the parts moving beneath the sensing mechanism. FIGS. 5A and 5B show how such a mechanism is implemented for gravity chutes and for belt transfer. FIG. 5A shows a part 51 which has slid down a gravity chute 50 (such as the chute 22 in FIG. 2 or the chute 45 in in FIG. 4). A solenoid 53 attached by a bracket 56 is spring-loaded by a spring 55 to extend a gate 54 into the path of the part 51, when actuated by an electrical signal on input wire 57 from a computer (not shown). The gate 54 has two positions: extended 54B and retracted 54A. When the part is stopped, the sensing by a sensing mechanism 52 is much more accurate.

FIG. 5B illustrates a similar solenoid actuating gate mechanism for a belt transport mechanism (such as the belt 3 in FIG. 1 or the belt 32 in FIG. 3). A part 61 moving on a belt 60 adjacent to a fence 68 is stopped in the sensing region of a sensing mechanism (not shown) by a solenoid 63 driving a gate 64 into its extended position 64B or its retracted position 64A; a spring 65 returns the gate to its retracted position while bracket 66 positions the solenoid 63 for proper operation.

Gates such as 54 and 64 can be pneumatically driven rather than electrically driven by devices common in the hard automation industry. Electrically driven gates are used for illustration because they are most commonly connected to computers through the use of relays. Similar solenoid-driven gates may be used for escapement or singulation mechanisms such as mechanism 12 in FIG. 1, mechanism 34A in FIG. 3 or mechanism 43 in FIG. 4. In any of these mechanisms, the computer actuates the gates only so long as to let a single part continue past the gate.

For shape measurement determination of somewhat lower accuracy, a detector is often required to insure that the sensing of the part 51 (FIG. 5A) occurs when the part is in the proper position relative to the sensing mechanism 52. In these applications a part presence detector replaces the part-stopping mechanisms in FIGS. 5A and 5B. Parts presence detectors include microswitches or proximity detectors which the part 51 actuates; such detectors are available from many suppliers as are optical trips wherein the part 51 breaks a beam of light. The latter method was used by Mellen ("Inspection of Moving Parts via Acoustic Phase Monitoring," M. S. Thesis, Mechanical Engineering Dept., M.I.T., June 1979, D. B. Mellen) in evaluating the accuracy of acoustic sensors on moving parts.

The sensing mechanism itself is the critical component of the parts sorting orienting systems shown in FIG. 1 through FIG. 4. The sensing mechanism is composed of an array of sensors which use either acoustic or electromagnetic wave variations as discussed in the Buckley U.S. Pat. Nos. 4,095,474 and 4,200,921. A brief summary of those sensors will now be discussed.

Acoustic sensors are composed of transmitter-receiver transducers such that sound waves are transmitted by the transmitter, interact with the part and are picked up by the receivers. FIG. 6A shows an array 70 composed of transmitter 71 and receivers 72 used to detect the shape of a part 74. Electrical signals input to transmitter 71 via contacts 75 are transduced into acoustic wave energy 76 which interacts with the part 74. The variations in wave energy 76 are received by receivers 72 whose output signal is available on contacts 73.

Electromagnetic sensors are shown in FIG. 6B (inductive sensors) and FIG. 6C (capacitive sensors). While sensors of this sort are quite common in such devices as proximity sensors, their use as a method of detecting a part's shape as part of a multi-element array of sensors using continuous wave energy and interpreted in the manner herein described is wholly new and innovative. A brief discussion of useful sensors and how they may be used in conjunction with the acoustic transducers just described follows. FIG. 6B shows an array 80 of inductive sensors 82 which are simply coils of wire. Electromagnetic wave energy 86 emanating from the sensors 82 interacts with a part 84. Electrical output signals from the sensors 82 is available on contacts 83. Inductive sensors such as those described are useful in determining the shape of a part 84 as well as certain magnetic properties of the part such as hardness and alloy.

FIG. 6C shows capacitive sensors 92 fixed to an array 90. The sensors 92 are simply conducting plates which can generate electromagnetic waves 96 which interact with a part 94. The interaction can be detected via electrical contacts 93 for interpretation by the computer. Capacitive sensors such as those described can detect other properties of the part 94 such as dielectric constant of certain plastics and the water content of paper products.

The electrical output signals on contacts 73 of the acoustic sensors 72 of FIG. 6A are sinusoidal signals whose amplitude and phase vary according to the shape of the part 74. These signals are subject to the details of the transduction method employed. In general, transducers 71 and 72 may operate by several well-known principles: electric diaphragms coupled to sensitive amplifiers, piezoceramic crystals coupled to sound-collecting diaphragms, "condenser" transducers coupled to a metal or plastic diaphragm and "voice-coil" transducers which couple coils embedded in a diaphragm in a driver coil close by.

For the electrical output of electromagnetic transducers (such as the sensors 82 and 92) to produce a similar phase and amplitude signal, several well known principles can be employed. In the following descriptions of these circuits, the generalized impedance Z will be used to represent either an inductor or a capacitor. FIG. 7A shows a self-impedance circuit 100 in which an impedance 101 is varied by its interaction through electromagnetic wave energy 106 with a part 105. The wave energy 106 is produced by a continuous wave electrical voltage source 103 driving current through resistor 102 and impedance 101. The voltage signal across terminals 104 is characterized by its amplitude and phase which is subsequently interpreted by a computer 200.

Typically the resistance 102 would be chosen such that the operating frequency of the circuit 100 is near the circuit's "break frequency" to maximize the change in amplitude and phase with changes in the shape of object 105. Other circuit elements can replace the resistor 102. For example, if a capacitor C, coupled with a resistor R, is substituted for the resistor 102 and the impedance 101 is an inductor L, tuned to the resonance of the LRC circuit, the amplitude and phase characteristics measured at the terminals 104 become quite sensitive to changes in the shape of part 105.

The circuit 100 in FIG. 7A is termed "self-impedance" because the sensor 101 both sends and receives electromagnetic wave energy. FIG. 7B is a circuit which is termed "transimpedance" because an impedance element 111 sends electromagnetic wave energy 116 and other impedances 112 receive the wave energy. An electrical voltage or current source of continuous waves 113 causes the impedance 111 to emanate wave energy 116 which interacts with object 115 to change the amplitude and phase signals output on terminals 114. For example, if the impedances 111 and 112 are coils, the transimpedence between the coils will vary depending on the shape of the object 115: the changes can be detected through amplitude and phase differences measured at the output terminals 114.

A third technique for detecting shape and other changes of a part is shown in a bridge circuit 120 in FIG. 7C. A continuous voltage or current source 123 drives the bridge composed of impedances 121, 122, 127 and 128. The bridge is balanced in the usual manner with impedances 121 and 122 chosen to be nearly equal to the impedances 127 and 128. Any change in the impedance 121 due to interaction with a part 125 through electromagnetic wave energy 126, causes a change in the amplitude and phase voltage signals on contacts 124.

It will be noted that all sensors, whether acoustic or electromagnetic, produce changes in the amplitude and phase of electrical signals to which they are connected. The sensors either produce wave energy or they receive wave energy which interacts with a part to convey information about the part. Usually the information is shape information but it can also include position and orientation information as well as certain other properties of the part. While each array shown has included only one type of sensor, in general any array can include several types of sensors all of which are interpreted in the same manner by the computer 200. Moreover, the sensors have been shown as simple linear arrays. In general, the sensors are deployed in a manner which best suits the class of parts which they are sensing. For example, inductive sensors for cylindrical parts have inductors through which the parts pass; acoustic sensors deployed in "phased arrays" become sensitive to specific regions of a part.

Now follows a brief discussion of the technique by which the computer interprets the amplitude and phase information from the various sensors. More detail on the method can be found in Buckley U.S. Pat. Nos. 4,095,474 and 4,200,921. FIG. 8 shows a parts sorting system 130 which details the function of the computer labeled 144. It will be noted that the system 130 is only a partial sub-system of the complete parts sorting and orienting mechanism of FIG. 1.

An object or a part 132A or 132B is transported down a transport mechanism such as a chute 131 from the ready position occupied by the part 132B. Solenoid gate mechanisms 146A and 146B, on signals 145 from the computer 144, ensures that only one part 132A is in the sensing region beneath the sensor array 148. In this example, the sensing array shown at 148 has a transmitting sensor 133 driven by the computer 144.

As discussed previously herein, the wave energy from the transmitting sensor (or transducer) 133 interacts with the part 132A and changes the amplitudes and phases of the continuous wave signals detected by the receiving sensors 134. These signals are fed to a multiplexor (MUX) 137 by connections 136, where one of the signals is chosen by the computer 144 to be analyzed. The connection 147 is a bus by which the computer 144 signals the multiplexor 137 which of the signals on connnections 136 is chosen. The chosen sinusoidal signal from the sensors 134 is fed via a connection 138 to an analog amplifier and filter 139 which amplifies or attenuates the signal (as required) and reduces noise at frequencies other than the sinusoidal operating frequency of the transmitted wave energy.

Next, the signal is converted to a digital value in a analog to digital converter ADC 140. The filtered sinusoidal signal is sampled at various time intervals as determined by a clock signal fed to the ADC 140 by the computer 144 via connection 142. The sampled digital values are sent to a digital filter 141 by a bus 149 where they are further filtered to remove noise at frequencies other than the transmitted wave energy frequency. Lastly, the filtered data is transmitted to the computer 144 via bus 143 for analysis. Analysis of the filtered data first requires that the data be converted to amplitude and phase information of the received wave energy for the chosen sensor 134. A Fourier transform algorithm, available in the literature, readily converts the digital values to amplitude and phase information. Note that in high performance systems which must operate at higher measurement rates, some of the elements shown in system 130 may be duplicated to allow their tasks to be done in parallel rather than serially. For example, a system which had two each MUX's 137 analog filters 139, ADC's 140 and digital filters 141 could make measurements twice as fast as system 130.

The computer 144 orchestrates the data gathering from sensors 134. First it transmits the operating frequency to the transmitter 133; it then directs one after another of the received sensor signals input from the MUX 137 to the analog amplifier and filter 139. The computer 144 also determines the timing and the duration of the data sampling in the ADC 140 and, further, receives and analyzes the amplitude and phase information from the digital filter 141. As each sensor signal, in turn, is processed, the computer 144, also stores the amplitude and phase information from previously processed sensor signals until all sensors 134 in the array 148 have been processed.

Given the phase and amplitude information from each sensor 134, analysis involves calculations of the general form:

$$X = g\left[\sum_{i=1}^{N} W_i f(A_i, \theta_i)\right] \text{ where}$$

X is the desired output
g is a functional relationship
$W_i$ is a weighting function chosen for each sensor
f is another functional relationship
$A_i$ is the amplitude of each sensor signal $\theta_i$ is the phase of each sensor signal
N is the number of sensors For example, in determining the diameter of a part 132A, the desired output X is the diameter. By choosing the weights $W_i$ to be proportional to each sensor's phase difference between a master part (of diameter D″ and with phase $\theta''_i$) and another part (whose diameter is D′ and with phase $\theta'_i$) the relationship simplifies to:

$$D = \sum_{i=1}^{N} W_i(\theta'_i - \theta''_i) + D''$$

$$W_i = \frac{D' - D''}{\theta'_i - \theta''_i}$$

Other relationships g and f are appropriate for other desired outputs such as determining one part from another or one orientation from another.

While the foregoing descriptions give ways to orient and sort parts, certain other apparatus and methods can improve the general resolution of the measurements, especially acoustic measurements.

The improved resolution techniques fall into three categories: temperature control of the medium, moving the medium and temperature control of the sensors. FIG. 9 shows a typical application where all three of the techniques are used. A parts sorter or orienting system 150 has a part 151 held in a chute 152 (viewed end-on). Wave energy is transmitted by a transmitter 153, interacts with the part 151 and is received by receivers 154 in an array 155, as has previously been discussed. The medium 156 through which the wave energy is transmitted is both moving and temperature-controlled.

The moving medium 156 is propelled by a fan 157 which forces the medium past the object 151. In practice, simply maintaining a gentle flow of the medium 156 can improve long-term phase and amplitude resolution by a factor of five or more. The present inventors believe that the moving medium 156 ensures that the average temperature of the medium 156 varies less quickly than if the medium is still. Since acoustic measurements (and to a lesser extent electromagnetic measurements) are influenced by the medium's temperature, temperature stability gives better phase measurement resolution.

In addition to simply moving the medium, even better long term phase measurements result if the medium's temperature is held fixed. In FIG. 9, a heating element 158 heats the medium 156 before flowing past object 151. A temperature sensor 159 detects the medium's temperature and controls the energy to the heating element 158 by a controller 160. Mixers and baffles 161 ensure that the medium 156 is thermally mixed before flowing past the object 151. By controlling the temperature of the medium 156, compensation for the change in the wavelength of acoustic wave energy (as discussed in Buckley U.S. Pat. No. 4,287,769) is not required. It will be noted that it is the temperature of the medium 156 which must be controlled, not that of object 151.

Although temperature changes of the medium are the principal reason for errors in measuring amplitude and phase (especially for acoustic wave energy), other medium changes can affect measurement resolution. For example, in certain capacitance sensors, the humidity of the medium can produce errors in the shape or orientation paramenters measured. Humidity control of the medium is one way of reducing these errors; humidity controls are standard industrial hardware available from several suppliers.

Another way of improving the amplitude and phase measurement of acoustic and electromagnetic sensors 153 and 154 is by holding fixed the temperature of the array 155 along with its sensors and 154. The sensors 153 and 154 are mounted on a heat conducting block, such as aluminum, with good thermal contact between sensors and block. A temperature sensor 162 senses the block's temperature and controls the energy to a heating element 163 via a temperature controller 164. The sensors 153 and 154 are held at a temperature higher than would be encountered in the field such that heat must always be added to the array 155 to hold its temperature fixed. By keeping the sensors 153 and 154 at a fixed temperature, drift of amplitude and phase measurements can be all but eliminated. Since each of the sensors 53 and 154 seldom has the same measurement drift with temperature as the other, holding the array 155 at a fixed temperature eliminates the cost of matched sensors.

A last method for compensating for changes in the medium is discussed in Buckley U.S. Pat. No. 4,287,769. In that method, certain property changes of the medium cause a corresponding (and known) change in the wavelength of the continuous wave energy. Changing the frequency of the transmitted wave energy by the proper amount ensures that the phase and amplitude information remains constant despite property change of the medium. In the cases where the property changes are temperature or humidity, temperature or humidity sensors can determine the amount of frequency change required. For this and other property changes of the medium, the frequency can also be corrected by comparing amplitude and phase information made with no part in the sensing region and adjusting the frequency until no change appears in the phase and amplitude information.

Further modifications of the invention herein disclosed will occur to persons skilled in the art and all such modifications are deemed to be within the scope of the invention as defined by the appended claims.

What is claimed is:

1. Apparatus for parts sorting, that comprises:
    parts feeding means to feed a part into a sensing region;
    means for transmitting continuous wave energy of a single frequency through the medium surrounding the part in the sensing region where wave energy ineracts with said part;
    sensor means positioned to detect wave energy that interacts with the part by virtue of the wave energy directed thereupon, said sensor means comprising a multiplicity of spaced-apart sensors disposed in an array to receive the wave energy at a multiplicity of places after interaction with the part and propagation through said medium to the sensor means;
    means for processing the received wave energy into information for each sensor of the sensor means;
    means for analyzing said information from the multiplicity of sensors and operable to generate a single sampling signal output representative of a characteristic of said part; and
    means for sorting connected to receive said single sampling signal output and operable to sort said part in response to said characteristic;
    in which the continuous wave energy is sinusoidal wave energy of a single frequency and in which the multiplicity of spaced-apart sensors are sensitive to specific regions of the part, each sensor providing an electrical output containing at least one of amplitude and phase information which is weighted for each sensor on the basis of the characteristic being sensed, said electrical output being sinusoidal signals whose amplitude and phase vary according to the characteristics of the part.

2. Apparatus as in claim 1 wherein said characteristic is the orientation of said part and wherein the means for analyzing is operable to apply a weighting function to said information.

3. Apparatus as in claim 1 wherein said transmitted wave energy is acoustic wave energy and electromagnetic wave energy, a portion of said sensors being arrayed acoustic sensors that receive the acoustic wave energy, the remainder of said sensors being arravyed electromagnetic wave sensors that receive the electromagnetic wave energy.

4. Apparatus as in claim 1 wherein said feeding means allows only one said part at a time to enter said sensing region.

5. Apparatus as in claim 1 wherein sorting is accomplished by a parts manipulating device whose actions are changed in response to said characteristic.

6. Apparatus as in claim 1 wherein said means for processing comprises multiplexing means such that the signals from several of said sensors are processed sequentially.

7. Apparatus as in claim 1 wherein said means for processing comprises multiple processing circuits which simultaneously obtain said information from at least two of said sensors.

8. Apparatus as in claim 1 wherein said means for processing includes filtering means to reject frequency components of said received wave energy which are not at said single transmitted frequency of wave energy.

9. Apparatus as in claim 8 wherein said filtering is accomplished by combining sequential digital samples of said received wave energy.

10. Apparatus as in claim 1 that includes means for maintaining fixed a physical property of the medium.

11. Apparatus as in claim 10 wherein the property is the temperature of the medium.

12. Apparatus as in claim 1 wherein changes in at least one of the properties of the medium in said sensing region through which said wave energy is transmitted is compensated for by changing the single frequency of continuous wave transmission.

13. Apparatus as in claim 1 wherein the temperature of said multiplicity of sensors is held fixed by temperature control means.

14. Apparatus as in claim 1 wherein said characteristic is the shape of said part.

15. Apparatus as in claim 1 which includes a parts storage means for supplying said parts feeding means.

16. Apparatus as in claim 1 in which the means for transmitting continuous wave energy includes means to transmit electromagnetic wave energy through said medium and in which the sensor means comprises an array of electromagnetic wave energy sensors.

17. Apparatus as in claim 16 in which the array of electromagnetic wave sensors comprises several inductive sensors which receive the electromagnetic wave energy transmitted from the part back through the medium to provide a signal which contains information with respect to an electromagnetic characteristic of the part and in which the analyzing means is operable to generate a sampling signal which include the information with respect to the electromagnetic characteristic.

18. Apparatus as in claim 16 in which the array of electromagnetic wave sensors comprises several capacitive sensors which receive the electromagnetic wave energy transmitted from the part back through the medium to provide a signal which contains information with respect to an electromagnetic characteristic of the part and in which the analyzing means is operable to generate a sampling signal which includes the information with respect to the electromagnetic characteristic.

19. Appartus according to claim 1 in which the continuous wave energy is sinusoidal acoustic wave energy of a single frequency and in which the multiplicity of spaced-apart sensors are acoustic sensors deployed in a linear array.

20. Apparatus for parts sorting, that comprises:
parts feeding means to feed a part into a sensing region;
means for transmitting continuous wave energy of a single frequency through the meduim surrounding the part in the sensing region where the wave energy interacts with said part;
sensor means positioned to detect wave energy that interacts with the part by virtue of the wave energy directed thereupon, said sensor means comprising a multiplicity of spaced-apart sensors disposed in an array to receive the wave energy at a multiplicity of places after interaction with the part and proragation through said medium to the sensor means;
means for processing the received wave energy into information for each sensor of the sensor means;
means for analvzing said information from the multiplicity of sensors and operable to generate a single sampling signal output representative of a characteristic of said part; and
means for sorting connected to receive said single sampling signal output and operable to sort said part in response to said characteristic;
wherein said means for sorting includes means for recycling a portion of the parts to the parts feeding means, based upon said characteristic, wherein the single sampling signal is designated X, and wherein the means for analyzing the information from the combined sensors of the sensing means to derive the single sampling signal X uses calculations in accordance with the general form:

$$X = g\left[\sum_{i=1}^{N} W_i f(A_i, \theta_i)\right], \text{ where}$$

X is the desired output.
g is a functional relationship
$W_i$ is a weighting function chosen for each sensor,
f is another functional relationship,
$A_i$ is the amplitude of each sensor signal,
$\theta_i$ is the phase of each sensor signal, and
N is the number of sensors.

21. Apparatus as in claim 20 wherein said characteristic is the orientation of said part.

22. Apparatus for parts sorting, that comprises:
parts feeding means to feed a part into a sensing region;
means for transmitting continous wave energy of a single frequency through the medium surrounding the part in the sensing region where the wave energy interacts with said part;
sensor means positioned to detect wave energy that interacts with the part by virtue of the wave energy directed thereupon, said sensor means comprising a multiplicity of spaced-apart sensors disposed in an array to receive the wave energy at a multiplicity of places after interaction with the part and propagation through said medium to the sensor means;
means for processing the received wave energy into information for each sensor means;
means for analyzing said information from the multiplicity of sensors operable to generate a single sampling signal output representative of a characteristic of said part; and
means for sorting connected to receive said sampling signal output and operable to said part in response to said characterisic;
wherein the medium in said sensing region through which said wave energy is transmitted is made to flow.

23. Apparatus according to claim 22 that includes means to control the temperature of said medium.

24. Apparatus for achieving at least one of sorting and orienting objects, that comprises:
object feeding means to feed an object into a sensing region;
means for transmitting continuous wave energy of a narrow-frequency band into the sensing region where the wave energy interacts with the object to provide scattered wave energy;
sensor means comprising a multiplicity of spaced sensors disposed at a multiplicity of places in an array to receive the scattered wave energy and adapted to provide electric signals representative of the scattered wave energy;
process means connected to receive said electric signals and operable to receive therefrom at least one of amplitude information and phase information with respect to each sensor of the multiplicity of sensors;
analyzing means to analyze said at least one of the amplitude information and the phase information to extract therefrom intelligence that identifies a geometry parameter of the part; and
means for achieving at least one of sorting and orienting of the part on the basis of the at least one parameter so identified;
said continuous wave energy being sinusoidal acoustic wave energy of a single frequency, in which the multiplicity of spaced-apart sensors being acoustic sensors deployed in an array to render the arrayed sensors sensitive to specific regions of the part, each sensor providing an electrical output containing at lease one of amplitude and phase information which is weighted for each sensor on the basis of the characteristic being sensed, said electrical output being sinusoidal signals whose amplitude and phase vary according to the geometric characteristics of the part.

25. A method of sorting parts by size, surface and shape characteristics and orientation for (automatic) continuous assembly of apparatus, that comprises:
(a) feeding a part into a predetermined three-dimensional sensing zone;
(b) transmitting continuous wave energy at a single frequency into said sensing zone for interaction with the part positioned therein;

(c) position a plurality of continuous wave energy sensors adjacent to said zone;

(d) separately detecting at each of said sensors the resultant wave energy at said single frequency in said sensing zone after interaction with said part;

(e) generating a sampling signal in response to a characteristic of at least one of the amplitude and phase of the detected wave energy for each of said sensors, which sampling signal is combined with sampling signals from the other sdnsors to provide a single combined sampling signal;

(f) comparing differences between a pre-established signal and said single combined sampling signal to determine whether the part is within acceptable tolerances in terms of size, shape characteristic and orientation; and (g) sorting said part in accordance with the compared differences;

said continuous wave energy being sinusoidal acoustic wave energy of a single frequency, the spaced-apart sensors being acoustic sensors deployed in an array to render the arrayed sensors sensitive to specific regions of the part, each sensor providing electrical output containing at least one of amplitude and phase information which is weighted for each sensor on the basis of the characteristic being sensed, said electrical output being sinusoidal signals whose amplitude and phase vary according to the geometric characteristics of the part.

26. A method of sorting parts for robotic assembly into apparatus as a single component and at a given location, which comprises:

position a part for a part for such assembly into a continuous wave field having a known single frequency and known amplitude, said field being generated at a first location to interact with said part;

sensing the direct, reflected and refracted wave energy within said field at said known frequency using sensors disposed at a multiplicity of locations spaced apart from each other and from said first location;

generating a single combined signal derived from the sensed wave energy from said multiplicity of locations;

comparing the generated signal to a standard signal measured by the same steps for an acceptable part; and rejecting or accepting said part for such robotic assembly on the basis of the comparison between the generated signal and the standard signal;

said continuous wave energy being sinusoidal wave energy of a single frequency, the spaced sensors being sensors deployed in an array to render the arrayed sensors sensitive to regions of the part, each sensor providing an electrical output containing at least one of amplitude and phase information which is weighted for each sensor on the basis of the characteristic being sensed, said electrical output being sinusoidal signals whose amplitude and phase vary according to said characteristic.

* * * * *